(12) United States Patent
Huang et al.

(10) Patent No.: US 9,927,367 B2
(45) Date of Patent: Mar. 27, 2018

(54) APPARATUS AND METHODS FOR WELD MEASUREMENT

(71) Applicant: Arconic Inc., Pittsburgh, PA (US)

(72) Inventors: Wei Huang, Monroeville, PA (US); Michael Globig, New Kensington, PA (US); Donald J. Spinella, Greensburgh, PA (US); K. Rao Vemuri, Murrysville, PA (US)

(73) Assignee: ARCONIC INC., Pittsburgh, PA (US)

( * ) Notice: Subject to any disclaimer, the term of this patent is extended or adjusted under 35 U.S.C. 154(b) by 323 days.

(21) Appl. No.: 14/702,204

(22) Filed: May 1, 2015

(65) Prior Publication Data

US 2015/0317786 A1 Nov. 5, 2015

Related U.S. Application Data

(60) Provisional application No. 61/988,641, filed on May 5, 2014.

(51) Int. Cl.
*H04N 5/232* (2006.01)
*G01N 21/88* (2006.01)
(Continued)

(52) U.S. Cl.
CPC ........... *G01N 21/88* (2013.01); *G06T 7/0006* (2013.01); *H04N 5/2252* (2013.01);
(Continued)

(58) Field of Classification Search
CPC ........... G06T 7/80; G06T 7/62; G06T 7/0006; G06T 7/0004; G06T 2207/10004; G01N 21/88
(Continued)

(56) References Cited

U.S. PATENT DOCUMENTS 2,656,760 A * 10/1953 Bowerman ............ G02B 21/24
16/70
4,677,473 A * 6/1987 Okamoto ......... G01N 21/95684
228/105

(Continued)

FOREIGN PATENT DOCUMENTS

CN 102656444 A 9/2012
CN 103076330 A 5/2013
(Continued)

OTHER PUBLICATIONS

Konishi et al, Machine generated translation of JP 2012-103136 A, May 2012.*
(Continued)

*Primary Examiner* — David Harvey
(74) *Attorney, Agent, or Firm* — Greenberg Traurig, LLP

(57) ABSTRACT

An apparatus and method for measuring broken spot weld artifacts has a framework for supporting a light and a plurality of cameras for acquiring controlled images of a specimen with minimal distortion and parallax. The framework holds the specimen flat and in a reproducible position, controlling movement while imaging. The image data is received in a computer programmed with image processing software capable of isolating and measuring the artifacts. A calibration standard is used to correct for aberrations.

17 Claims, 19 Drawing Sheets

(51) Int. Cl.
*G06T 7/00* (2017.01)
*H04N 5/225* (2006.01)
*H04N 5/247* (2006.01)

(52) U.S. Cl.
CPC ....... *H04N 5/2256* (2013.01); *H04N 5/23229* (2013.01); *H04N 5/247* (2013.01); *G06T 2207/10004* (2013.01)

(58) Field of Classification Search
USPC ........................................................ 348/92
See application file for complete search history.

(56) References Cited

U.S. PATENT DOCUMENTS

| | | | | |
|---|---|---|---|---|
| 5,060,065 | A * | 10/1991 | Wasserman | G01N 21/8806 348/126 |
| 5,245,421 | A * | 9/1993 | Robertson | H04N 7/18 348/126 |
| 5,461,417 | A * | 10/1995 | White | G01N 21/8806 348/125 |
| 5,648,619 | A * | 7/1997 | Gustafsson | G01B 11/24 73/865.8 |
| 5,726,705 | A * | 3/1998 | Imanishi | G01N 21/8806 348/92 |
| 5,862,973 | A * | 1/1999 | Wasserman | B23K 31/12 228/103 |
| 6,033,087 | A * | 3/2000 | Shozo | G01N 21/8806 362/19 |
| 6,262,387 | B1 | 7/2001 | Chang | |
| 6,273,338 | B1 * | 8/2001 | White | G01N 21/8806 235/455 |
| 6,563,575 | B1 | 5/2003 | Nichols | G01N 21/8806 356/237.1 |
| 6,667,762 | B1 * | 12/2003 | Bouvier | G01N 21/8806 348/131 |
| 7,075,565 | B1 * | 7/2006 | Raymond | G01N 21/95684 348/126 |
| 7,664,311 | B2 | 2/2010 | Yamasaki | G01B 11/14 382/149 |
| 8,330,809 | B2 * | 12/2012 | Thomas | A01K 43/00 348/89 |
| 8,487,999 | B2 * | 7/2013 | Yoo | G01B 11/24 348/153 |
| 9,423,245 | B2 * | 8/2016 | Keranen | G01B 11/245 |
| 2002/0134817 | A1 * | 9/2002 | Shepard | G01N 25/72 228/105 |
| 2003/0234239 | A1 * | 12/2003 | Lee | B23K 11/24 219/109 |
| 2005/0231713 | A1 | 10/2005 | Owen | |
| 2006/0000989 | A1 * | 1/2006 | Kuriyama | G01N 21/8806 250/559.34 |
| 2008/0137088 | A1 * | 6/2008 | Wagner | G01B 11/24 356/446 |
| 2009/0128625 | A1 * | 5/2009 | Loipetsberger | G01N 21/8806 348/90 |
| 2009/0190824 | A1 * | 7/2009 | Niimura | G01N 21/8901 382/141 |
| 2010/0259746 | A1 * | 10/2010 | Ohnishi | G01B 11/245 356/4.01 |
| 2011/0069154 | A1 * | 3/2011 | Case | G01N 21/9501 348/46 |
| 2012/0044504 | A1 * | 2/2012 | Ohnishi | G01B 11/24 356/602 |
| 2015/0253129 | A1 * | 9/2015 | Ohnishi | G01B 11/24 348/87 |

FOREIGN PATENT DOCUMENTS

| | | | |
|---|---|---|---|
| CN | 204944428 U | | 1/2016 |
| JP | 407185832 A | * | 7/1995 |
| JP | 2725582 B2 | * | 3/1998 |
| JP | 2008-102103 A | * | 5/2008 |
| JP | 2009-031228 A | * | 2/2009 |
| JP | 2010-025615 A | * | 2/2010 |
| JP | 2012-103136 A | * | 5/2012 |
| JP | 2012-103217 A | * | 5/2012 |
| JP | 2013221861 A | * | 10/2013 |
| WO | WO 91/06846 | * | 5/1991 |
| WO | 2010090605 A1 | | 8/2010 |
| WO | WO 2014/167566 | * | 10/2014 |

OTHER PUBLICATIONS

Reichert, C. et al., Inspecting RSW Electrodes and Welds with Laser-Based Imaging, Welding Journal, (Feb. 2007), pp. 38-45.
International Search Report and Written opinion of the International Searching Authority dated Aug. 10, 2015 in reference to International Application No. PCT/US15/28855.
National Instruments, "Particle Measurements"; NI Vision; Publication [online], 2010. [retrieved Jul. 14, 2015]. Retrieved from Internet; <URL:http://zone.ni.com/reference/en-XX/help/372916J-01/nivisionconcepts/particle_measurements/> pp. 1-10.

\* cited by examiner

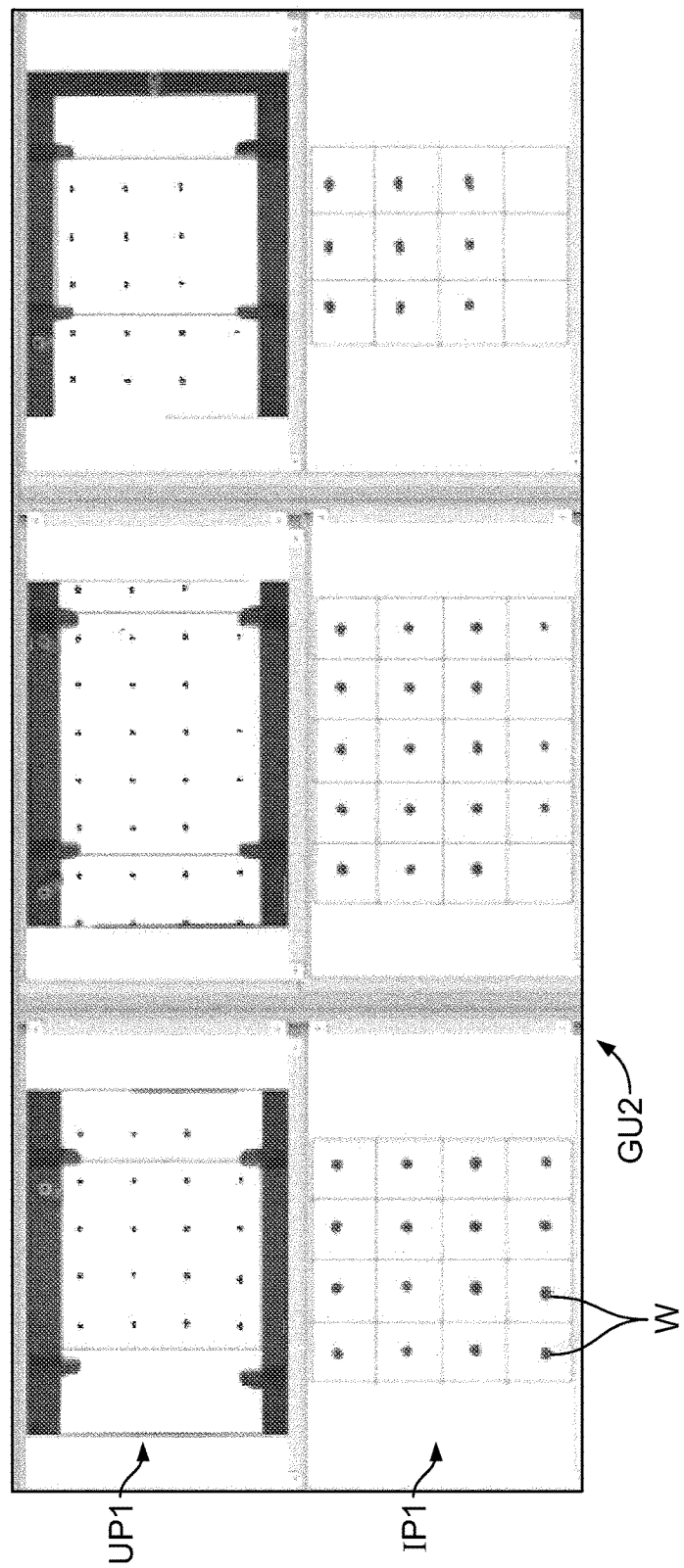

APPARATUS AND METHODS FOR WELD MEASUREMENT

CROSS-REFERENCE TO RELATED APPLICATIONS

The present application claims the benefit of U.S. Provisional Application No. 61/988,641, filed May 5, 2014, entitled Apparatus and Methods For Weld Measurement, the disclosure of which is incorporated by reference herein in its entirety for all purposes.

FIELD

The present invention relates to apparatus and methods for measuring welds, and more particularly, to measuring spot welds after destructive disassembly.

BACKGROUND

Methods for inspection of resistance spot welding (RSW) are known involving detecting spot weld formation, evaluating spot weld quality, and predicting the end of electrode life. In one approach, the weld joint is broken and the weld dimensions are measured manually, e.g., by a caliper. The weld dimensions and appearance may also be evaluated by comparing the weld fracture appearance to standards of a classification system, such as, American Welding Society, AWS D8.2, Specification for Automotive Weld Quality-Resistance Spot Welding of Aluminum. Laser-based inspection systems have also been developed for the inspection of resistance spot welding of steel. Notwithstanding, improved and/or alternative methods and apparatus for inspecting welds remain desirable.

SUMMARY

The disclosed subject matter relates to an apparatus for inspecting a specimen with at least one bond artifact and has a light capable of illuminating the specimen, a camera capable of capturing a digital image of the specimen, and a computer capable of receiving the digital image of the specimen from the camera and programmed with an image processing program capable of measuring the bond artifact and reporting the result of measuring to a user.

In accordance with another embodiment, a framework holds the light, camera and the specimen relative to one another.

In accordance with another embodiment, the framework includes a table that is capable of supporting the specimen in front of the camera and the light.

In accordance with another embodiment, the framework further has a specimen holder capable of pressing the specimen against the table.

In accordance with another embodiment, the specimen holder includes a plurality of inwardly extended fingers mounted on a frame that is capable of being selectively positioned between a position above the specimen and a position pressing the specimen against the table.

In accordance with another embodiment, the table is slidably coupled to the framework and is capable of assuming a position below the camera and a position distal to the camera permitting the specimen to be placed on the table, pressed down by the fingers and subsequently slid under the camera.

In accordance with another embodiment, the light has a diffuser hood with an aperture therein through which a lens of the camera may be extended.

In accordance with another embodiment, the camera is a first camera and further comprising at least one additional camera to define a plurality of cameras and wherein the diffuser hood has a plurality of apertures therein for admitting a lens of each of the plurality of cameras there through, each of the plurality of cameras capable of acquiring an image of the specimen within a field of view of the camera, the field of view of each camera differing from the field of view of the other cameras of the plurality of cameras.

In accordance with another embodiment, the plurality of cameras includes at least three cameras.

In accordance with another embodiment, the bond artifact is an artifact of a spot weld and further comprising a calibration standard having dimensions allowing the calibration standard to be placed on the table as the specimen is placed, the calibration standard having a plurality of spaced dots approximating a pattern of spot welds.

In accordance with another embodiment, a method for inspecting a specimen with at least one bond artifact, includes: illuminating the specimen; acquiring digital image data of the specimen and the bond artifact with a camera; receiving the digital image data of the specimen from the camera into a computer programmed with an image processing program; measuring the at least one bond artifact as represented in the image data; and reporting the result of the step of measuring to a user.

In accordance with another embodiment, the computer controls the camera during the step of acquiring, including a length of exposure of the specimen.

In accordance with another embodiment, further including the step of applying paint to the at least one bond artifact before the step of acquiring, the paint increasing the contrast of the bond artifact with the remainder of the specimen proximate the artifact.

In accordance with another embodiment, further including the step of flattening the specimen prior to the step of acquiring.

In accordance with another embodiment, further including acquiring digital image data of a calibration standard with the camera and receiving the digital image data of the calibration standard in the computer, and further receiving dimension data pertaining to the pattern on the calibration standard and comparing the dimension data and the digital image data, and then calculating a correction matrix to compensate for divergence of the image data from the dimension data.

In accordance with another embodiment, further including the step of applying the correction matrix to image data associated with image data of the specimen acquired during the step of acquiring.

In accordance with another embodiment, further including the steps of choosing a region of interest in the digital image data acquired during the step of acquiring and filtering insignificant areas from the image data.

In accordance with another embodiment, further including the steps of detecting an edge of the artifact and calculating the area and the max Feret diameter of the artifact.

In accordance with another embodiment, further including the steps of thresholding the grayscale values of the image data of the specimen against a pre-determined threshold criteria, filling holes in the image data and eliminating particles with a value less than or equal to the threshold.

In accordance with another embodiment, the at least one artifact is a plurality of artifacts of welds and further comprising the steps of generating a report of measurement data on the area of weld artifacts.

In accordance with another embodiment, a method for inspecting a specimen with at least one bond artifact, comprising:

positioning a calibration standard with a pattern before a camera;

illuminating the calibration standard;

acquiring digital image data of the calibration standard with the camera;

receiving the digital image data of the calibration standard in a computer;

further receiving dimension data pertaining to the pattern on the calibration standard in the computer;

comparing the dimension data and the digital image data, and then calculating a correction matrix to compensate for divergence of the image data of the calibration standard from the dimension data of the calibration standard;

positioning the specimen before the camera;

illuminating the specimen;

acquiring digital image data of the specimen and bond artifact with a camera;

receiving the digital image data of the specimen from the camera in the computer programmed with an image processing program;

applying the correction matrix to image data associated with image data of the specimen acquired during the step of acquiring;

identifying a region of interest in the image data of the specimen;

thresholding the image of the specimen relative to a criteria value;

filtering insignificant features from the image of the specimen;

detecting edges of the at least one bond artifact;

measuring the area and the max Feret diameter of the at least one bond artifact as represented in the image data; and reporting the result of the step of measuring to a user.

In accordance with another embodiment, the step of measuring includes calculating the max Feret diameter by identifying the distance between the two furthest away points on the edge of the bond artifact; ascertaining the area of the bond artifact; calculating the Waddle disk diameter of the circle with the same area as the bond artifact and calculating the ratio of the max Feret Diameter to the Waddle Disk diameter.

BRIEF DESCRIPTION OF THE DRAWINGS

For a more complete understanding of the present disclosure, reference is made to the following detailed description of exemplary embodiments considered in conjunction with the accompanying drawings.

FIGS. 16A-16C are screen shots of a graphical user interface of the system of FIG. 1 showing analysis of three different specimens in different gauges.

DETAILED DESCRIPTION OF EXEMPLARY EMBODIMENTS

Figure 1:
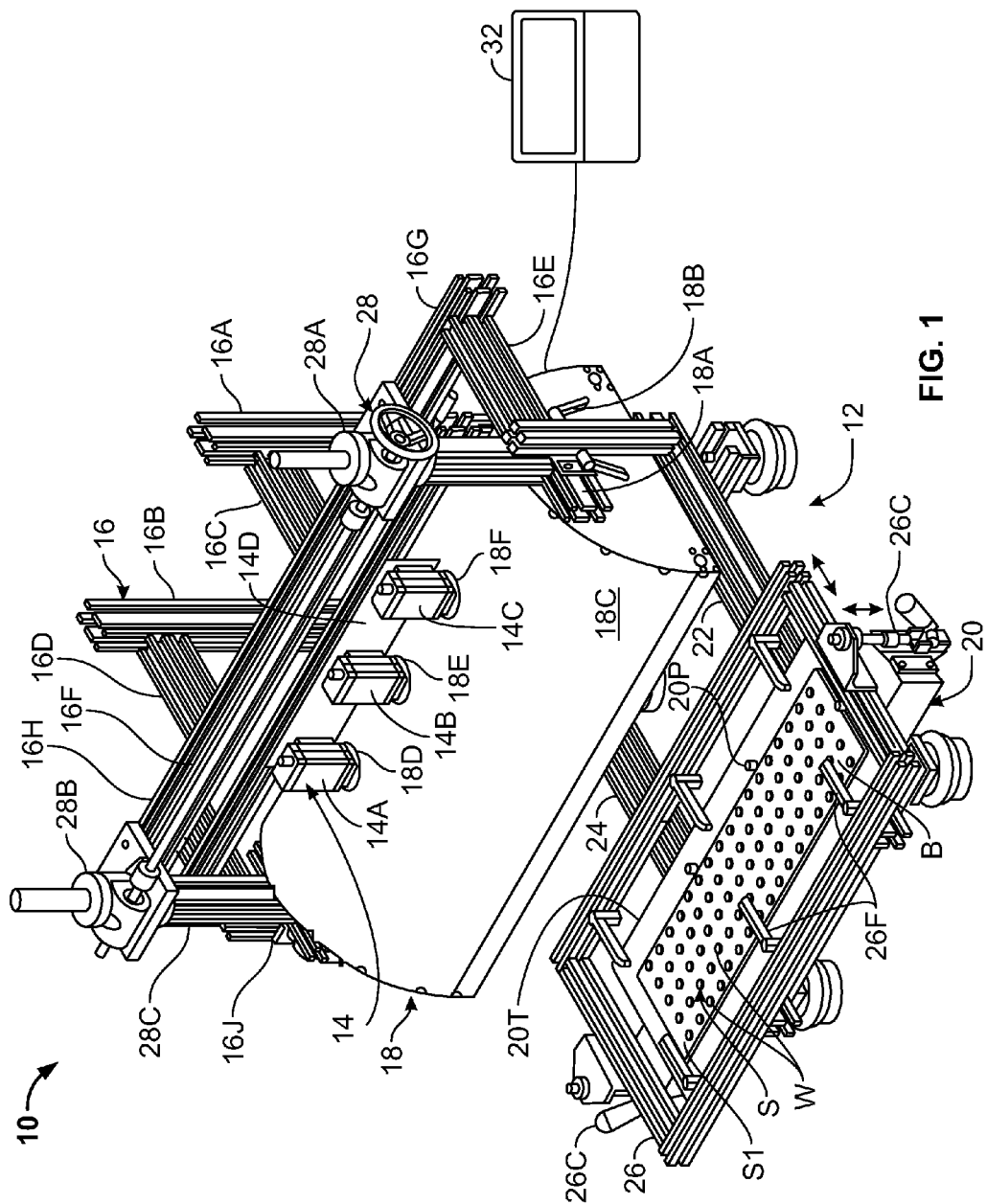
FIG. 1 is a perspective view a weld measurement system in accordance with an embodiment of the present disclosure.
Figure 2:
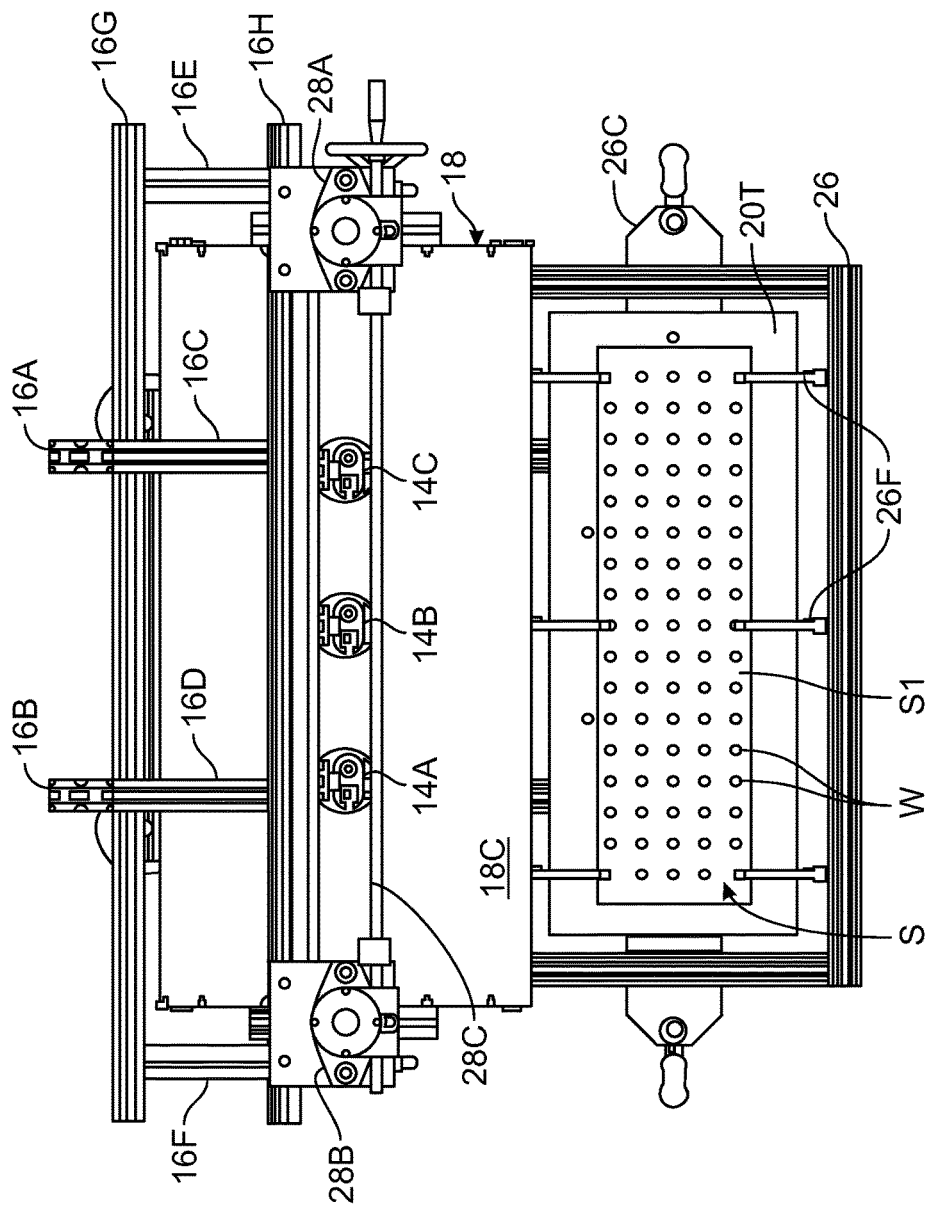
FIG. 2 is a plan view of the system of FIG. 1.
Figure 3:
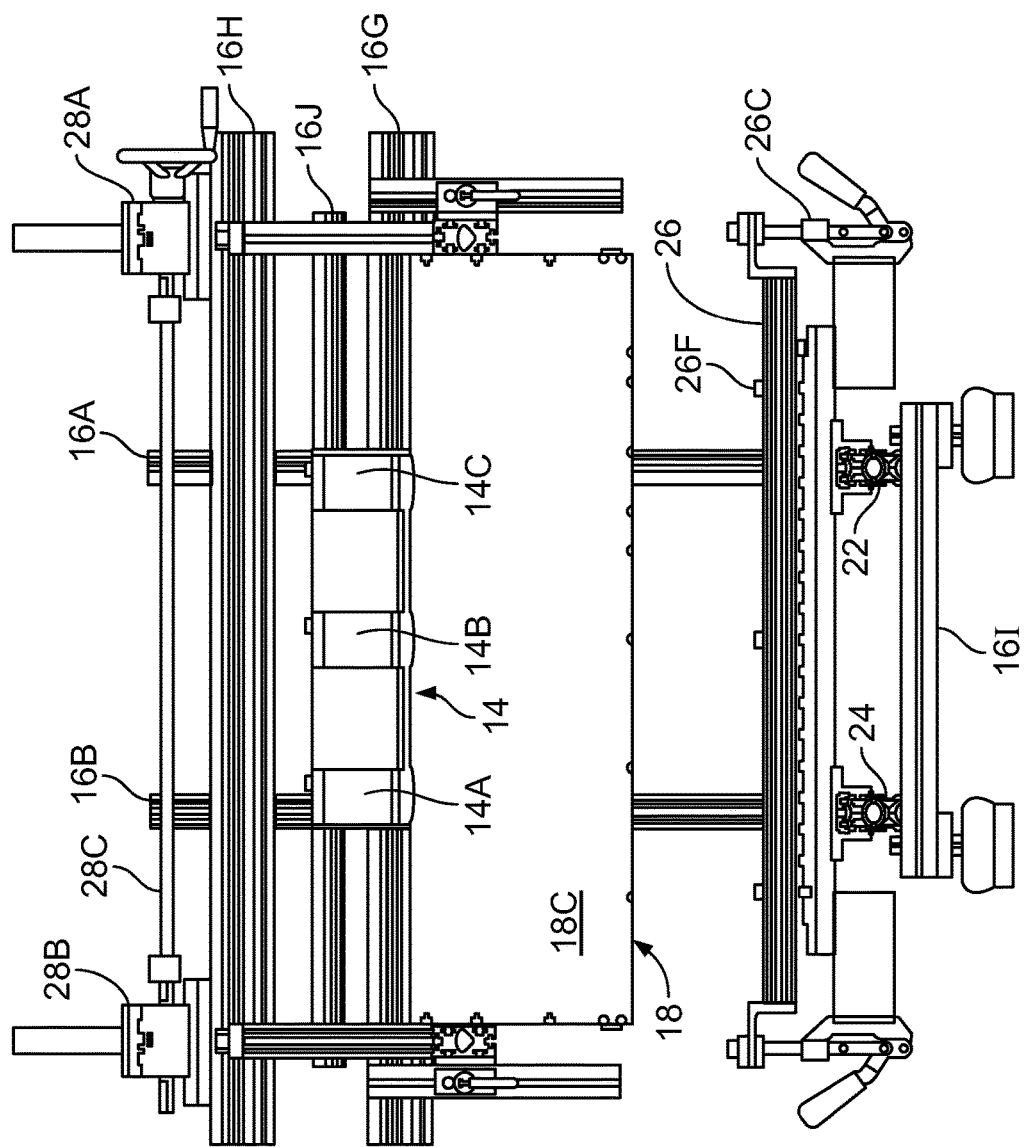
FIG. 3 is a front view of the system of FIG. 1.
Figure 4:
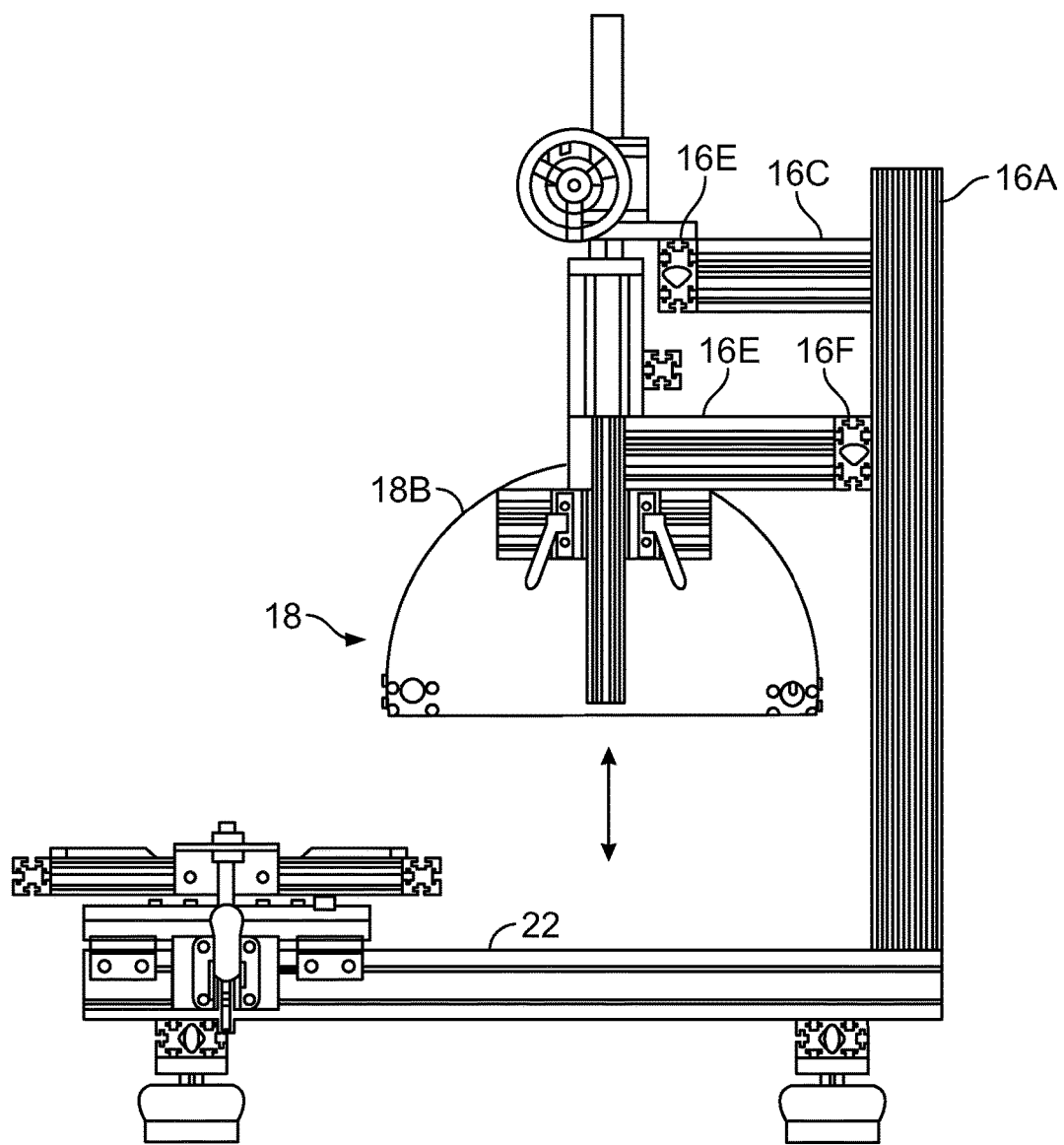
FIG. 4 is a side view of the system FIG. 1.

FIG. 1 shows a weld measurement system 10 having an imaging station 12, a camera assembly 14, a supporting framework 16 and a light assembly 18. A specimen support 20 with a specimen tray 20T receives a specimen S, e.g., a delaminated layer separated from a welded bilayer (not shown). The specimen exhibits artifacts of its prior welded condition, e.g., a plurality of holes, depressions or weld buttons W disposed on a surface S1 of the specimen S. The surface S1 on which the artifacts W are disposed would be non-welded metal, which would typically be relatively smooth and specular relative to the weld buttons W. When adapted to image specimens S having a consistent shape (length and width) a plurality of posts or positioning elements 20P may be disposed on the surface of the tray 20T to facilitate holding each specimen S at an optimal or workable position relative to the camera assembly 14 and light assembly 18. The tray 20T may be made from a black material, such as Delrin or may be painted black to offer minimal imaging presence and reflectivity. A specimen holder 26 having a frame 26A and a plurality of fingers 26F may be toggled up and down by toggle clamps 26C to a hold the specimen S by pressing the specimen S down against the tray 20T, to flatten the specimen S and provide a consistent, stable imaging position for the specimen S. The light assembly 18 is commercially available from Advanced Illumination, Inc. of Rochester, Vt., USA and includes a domed hood 18C that functions as a reflector and a diffuser to direct light generated by lights 18L1, 18L2 (diagrammatically shown in dotted lines) toward the specimen S. The hood 18C may be provided with a plurality of openings 18D, 18E, 18F through which the lenses of cameras 14A, 14B and 14C extend. The cameras may be three GigE cameras available from Allied Vision Technologies of Statroda, Germany. The cameras 14A, 14B, 14C may be arranged together as an assembly on a mounting plate 14D. Three cameras 14A, 14B, 14C are used to image an elongated sample S and minimize parallax and distortion in the images, such that a set of three images (one image for each camera 14A, 14B, 14C) may be taken simultaneously, the set of three images overlapping at their adjacent edges. More or fewer cameras 14A, etc., may be employed depending upon the length of the typical specimen S imaged. In a further alternative, a single camera 14A may be used to take a plurality of images of the specimen S at different locations, the camera 14A being moved parallel relative to the specimen S, e.g., on a slide or slides, taking images as it travels to positions directly over the specimen areas of interest. Surfaces of the weld measurement system 10 that do not participate in illuminating the specimen S may be painted a flat black color to minimize reflection and uneven illumination of the specimen.

When the specimen S is positioned on the specimen support 20 and the specimen holder 26 clamped down, the specimen support 20 may be slid on slide arms 22, 24 to an imaging position under the camera assembly 14 and the light assembly 18, where the specimen S may be imaged by the three cameras 14A, 14B, 14C. Each camera 14A, 14B, 14C may capture an image of part of the specimen S, e.g., a left portion, a middle portion and a right portion, respectively. The light assembly 18 may provide illumination that will saturate the specular specimen substrate S1 and highlight the rough surfaces of the weld buttons W. The contrast between the specimen S surface S1 and the weld buttons W promotes successful image processing which is directed to measuring and evaluating the dimensions of the weld buttons W. As shall be described below, the imaging system 10 has capabilities to enhance the contrast between the weld button W and the surface S1 of the specimen S.

The weld measurement system 10 includes a framework 16 with the a plurality of vertical uprights 16A, 16B, horizontal beams 16C, 16D, 16E, 16F and cross-beams 16G, 16H, 16I for supporting the camera assembly 14, light assembly 18 and the specimen support 20. The framework 16 may be adjustable to allow the relative positions of the camera assembly 14, the light assembly 18 and the specimen support 20 to be adjusted to optimize imaging. Jackscrew assembly 28 permits the camera assembly 14 and light assembly 18 to be raised and lowered relative to a specimen S and the specimen support 20. While the camera assembly and the light assembly are adjusted together, they may be arranged on the framework 16 to be separately adjustable in position. The jackscrew assembly 28 has individual jacks screws 28A, 28B connected by a bar 28C that enables both sides of the camera assembly 14 and light assembly 18 to be raised and lowered simultaneously and at the same rate. The light assembly 18 includes a light mount 18A and clamps 18B that may be used to secure the light assembly 18 at a given position after it has been moved by the jackscrew assembly 28. The weld measurement system 10 therefore provides a stable and repeatable positioning apparatus for positioning a specimen S relative to the light assembly 18 and the camera assembly 14. The framework 16 may be supported on vibration dampening feet 30 to insulate the weld measurement system 10 from vibrations of the supporting surface that could otherwise distort or blur images as they are captured by the camera assembly 14. A computer 32 may be used for controlling the light assembly 18 and the camera assembly 14 and is programmed with image processing software that presents a user interface that allows an operator to control the weld measurement system 10 and communicates imaging results and analysis to the user. In one embodiment, the imaging software utilized on the computer 32 may be off-the-shelf image processing software, e.g., LabVIEW available from National Instruments of Austin, Tex.

Figure 5:
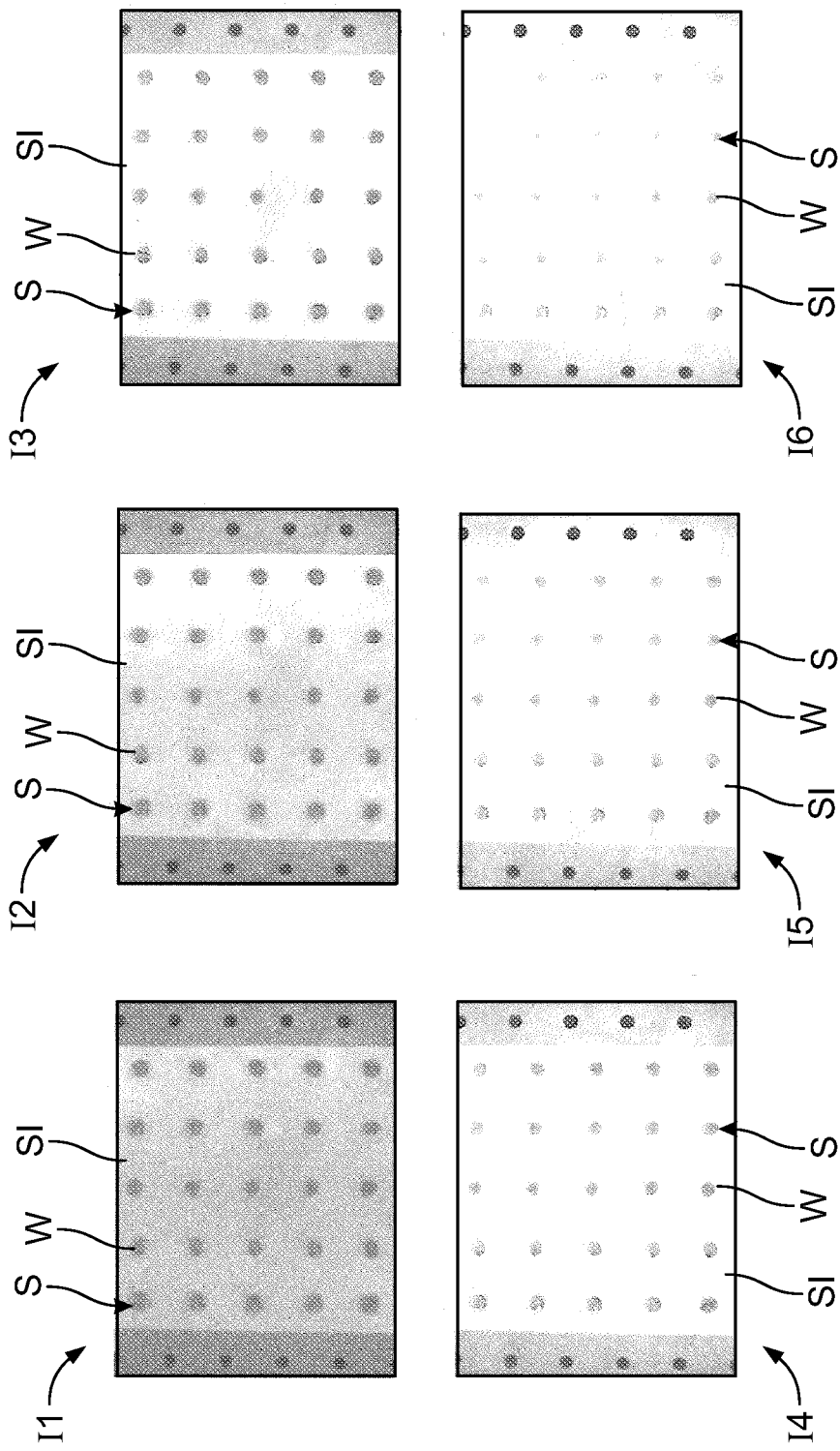
FIG. 5 is a collection of images of a specimen taken by the system of FIG. 1 at different lengths of exposure time.

FIG. 5 shows a plurality of images I1-I6, which were acquired by capturing images of a specimen S with the camera assembly 14 of the weld measurement system 10 described above. The images I1-I6 show the effect of varying the exposure time from 8000 microseconds to 18000 microseconds. The different exposure times resulted in images with varying contrast between the weld button W and the surrounding substrate surface S1. The camera exposure time can be manually chosen through the user interface of the computer 32 to provide the best contrast between the weld buttons W and the surrounding substrate surface S1. Optionally, the camera exposure time may be automatically adjusted by the computer 32 and/or the camera, e.g., 14A to optimize the contrast level.

Figure 6A:
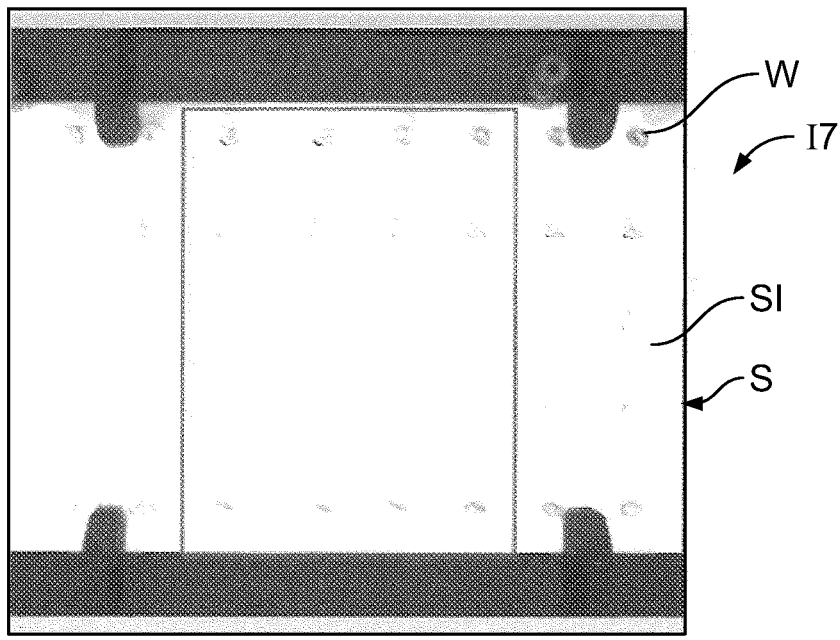
FIG. 6A is an image of a specimen taken by the system of FIG. 1 prior to enhancement by painting of the weld buttons.
Figure 6B:
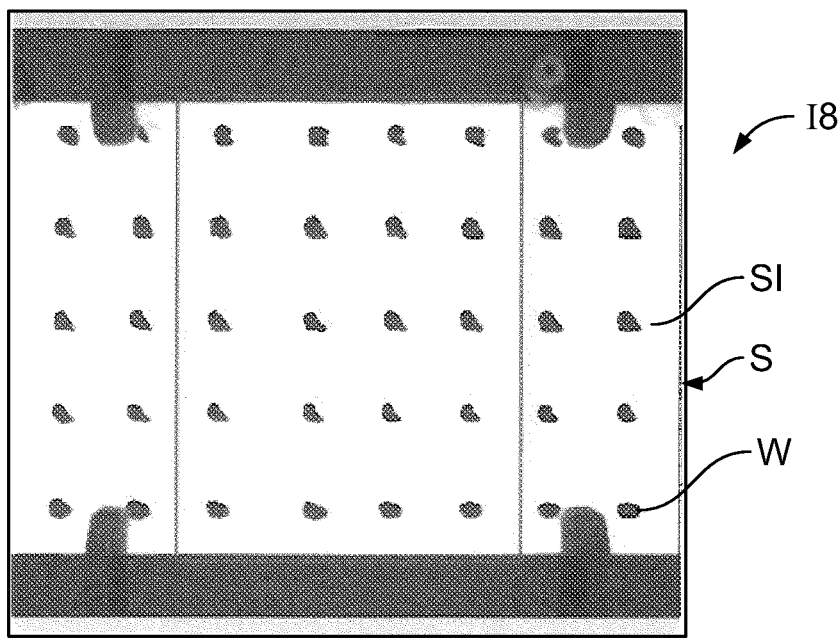
FIG. 6B is the image of FIG. 6A after enhancement by painting of the weld buttons.

FIG. 6A shows an image 17 of a specimen S taken by the weld measurement system 10 illustrating a lack of contrast between of the weld buttons W and the surrounding substrate surface S1. FIG. 6B shows an image 18 of a specimen S that was pre-processed before imaging by painting the upper surface of the weld buttons W. Painting can be done, e.g., with a roller that applies paint only to the upper surface of the weld buttons W and not to the surrounding substrate surface S1. The paint may be selected to present a contrast with the surface S1, e.g., a non-reflective black paint may be used to contrast with a shiny metallic surface S1. The paint may be applied manually or by an apparatus, e.g., the specimen S could be advanced by a conveyor belt below a paint applicator roller positioned at a predetermined distance from the specimen S to only contact the upper surface of the weld buttons W.

Because each camera 14A, 14B, 14C is subject to capturing images with distortions due to, e.g., aberrations in the camera lens or variations in sensitivity across the CCD array, the weld measurement system 10 may utilize an image calibration specimen SC (having the same appearance as the image SCIC of FIG. 7B), which has a geometrically regular and precise pattern, e.g., of dots having a consistent shape, diameter, color and spacing (equal, horizontal and vertical spacing distances from the center of each dot D on a background B), that can be used to identify and correct inherent aberrations caused by each camera 14A, 14B, 14C. The basic process is by acquiring an image of the calibration specimen SC and then noting where the image taken diverges from the actual known pattern with respect to feature spacing, size, color, etc. After these divergences are noted, a corrective matrix can be applied to any image subsequently taken with the same camera, e.g., 14A, to adjust the image for the aberrations intrinsic to the camera, and this may include the distortions attributable to camera position, e.g., parallax effect, as well as uneven lighting.

Figure 7A:
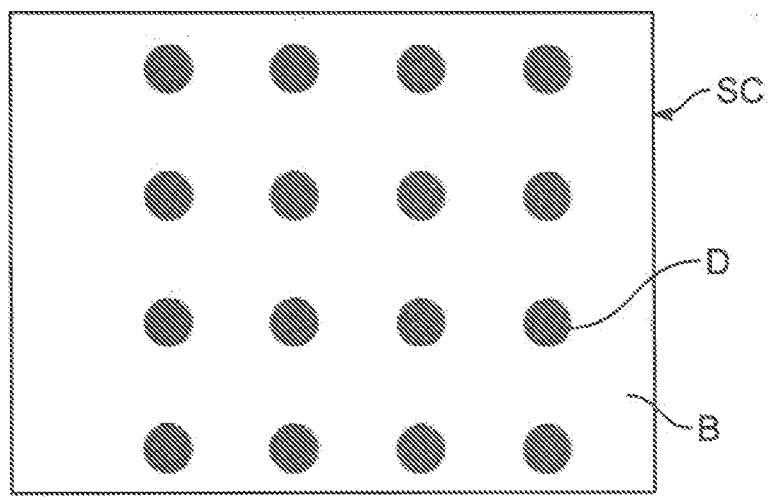
FIG. 7A is an image of a calibration standard of taken by the system of FIG. 1 prior to correction by image processing conducted by the system of FIG. 1.

FIG. 7A shows a calibration standard specimen SC having a regular pattern of black dots D on a white background B, e.g., as taken by one of the cameras 14A, 14B, 14C when the standard specimen is position on the specimen support in a position corresponding to a position that a specimen S of delaminated welded material would occupy when image acquisition is conducted. To guarantee accurate calibration, the top surface of the calibration standard specimen SC should be at the same height as the top surface of the weld buttons W of the specimens S that will be tested after calibration. The dots D of the calibration standard SC are evenly spaced and consistent in color and shape. LabVIEW vision development module provides standard calibration tool box/functions to perform an image calibration based on circular dots. (IMAQ calibration target to points-circular dots VI).

Figure 7B:
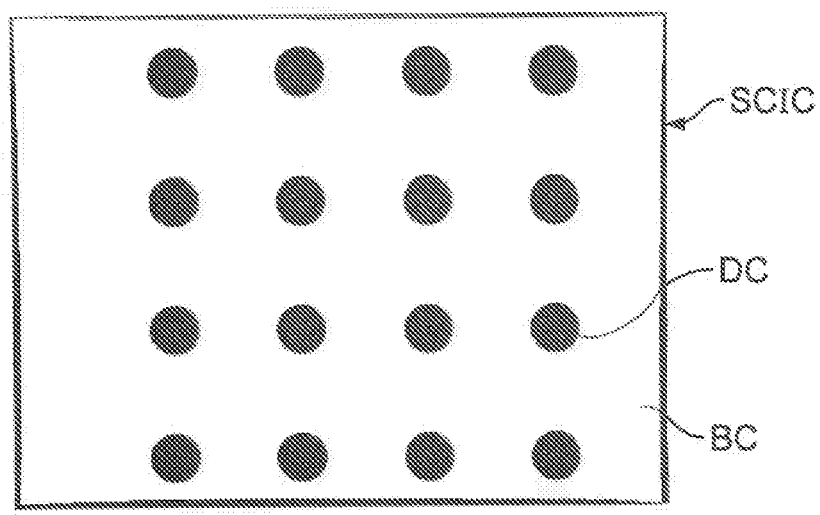
FIG. 7B is an image of the calibration standard of FIG. 7A after correction by image processing conducted by the system of FIG. 1.

FIG. 7B illustrates an image SCIC that results from the calibration of the image SC by the image processing software of the system 10. After the image of the calibration bar is taken by each camera 14A, 14B, 14C, the center of each dot is extracted through image processing and an array of image coordinates of the center of each dot is compared to the known, real-world coordinates of the calibration standard SC. A mapping matrix is then calculated to calibrate the image SC. This mapping matrix may be utilized to compensate for distortion due to a lens aberrations and perspective view. The image coordinates can then be mapped into real-world coordinates so measurement of the geometry of the weld buttons is feasible. The calculated mapping matrix can then be saved as a calibration image template which can then later be applied to correct images of specimens S and to calculate the extracted geometrical features of those specimens S.

Figure 8A:
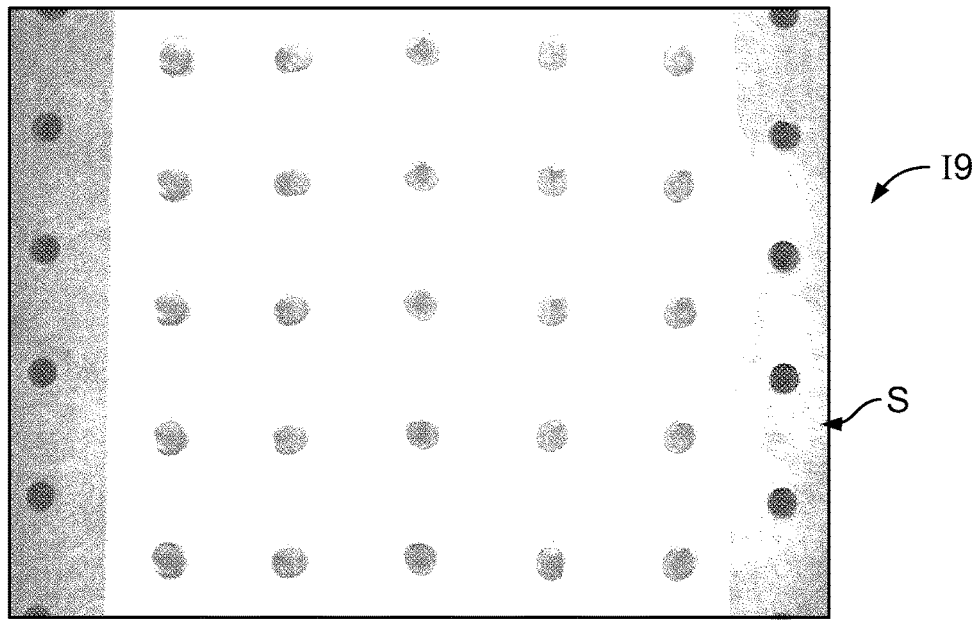
FIG. 8A is an image a specimen taken by the system of FIG. 1 prior to correction.
Figure 8B:
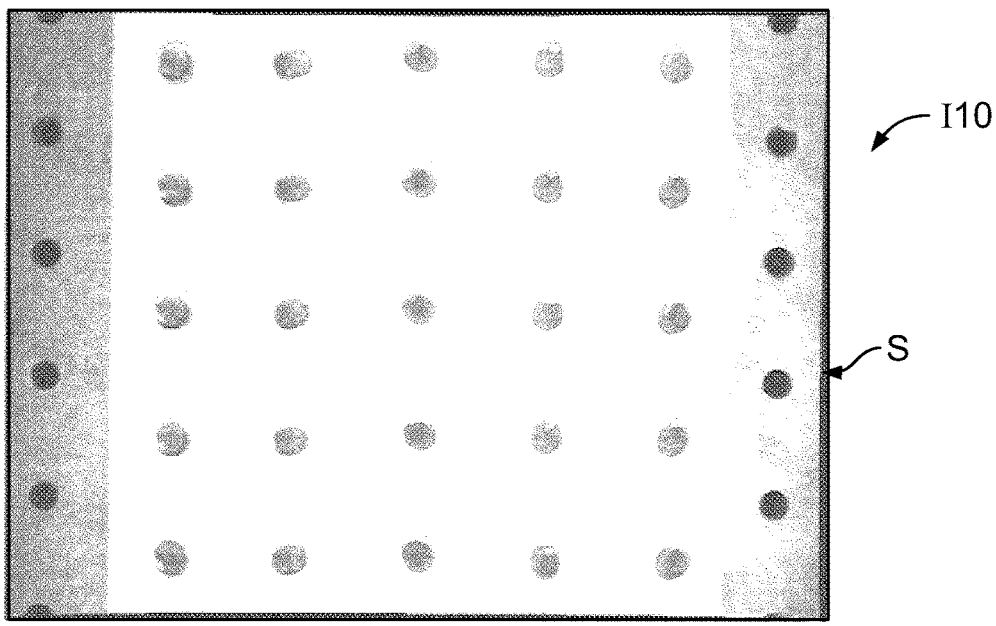
FIG. 8B is an image of the specimen of FIG. 8B after correction by image processing conducted by the system of FIG. 1.

FIG. 8A shows an image I9 of a specimen S prior to applying the calibration matrix to correct for aberrations. FIG. 8B shows the image of I10, which represents a corrected image I9 of FIG. 8A, after the mapping matrix is applied.

Figure 9:
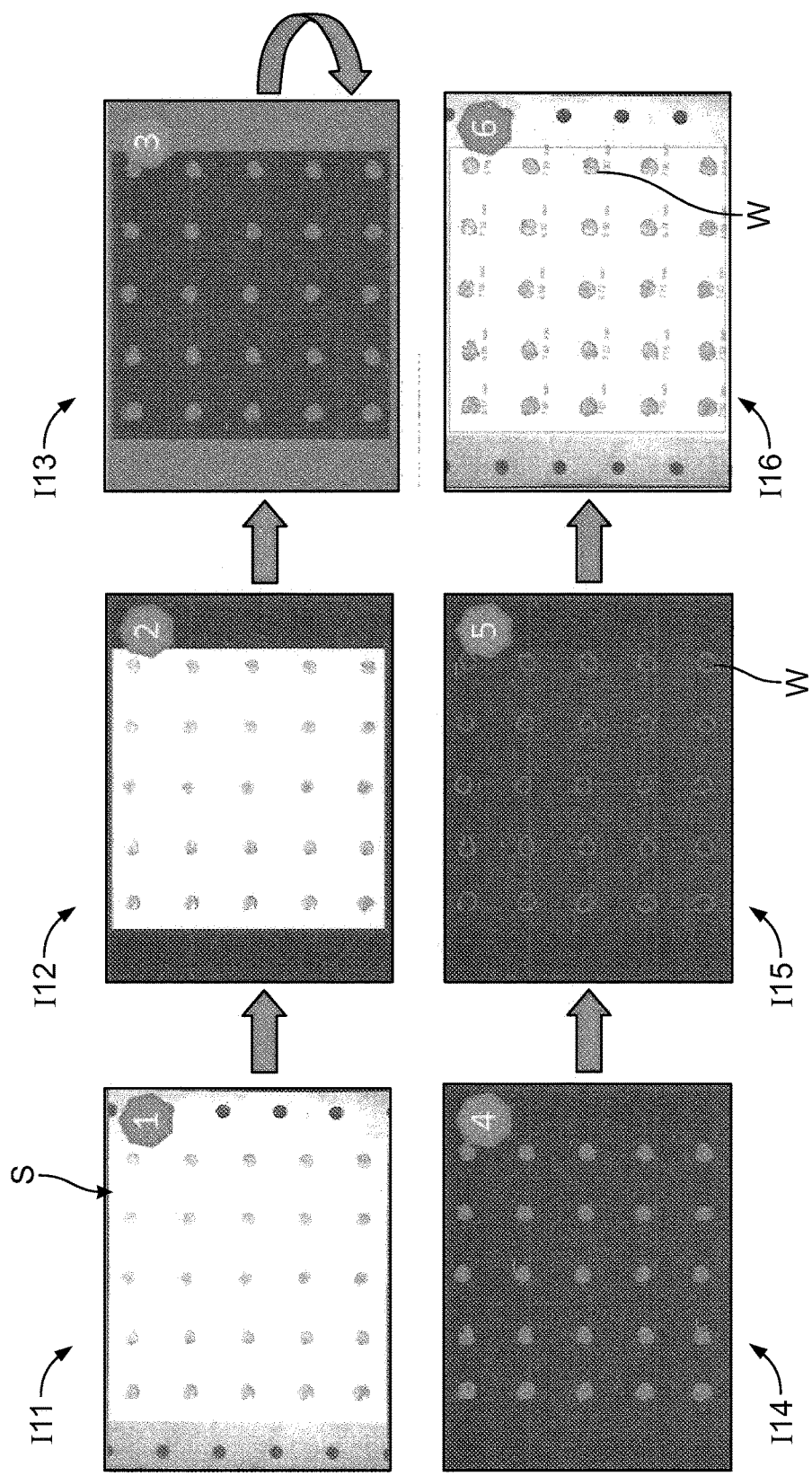
FIG. 9 is a sequence of images of specimens showing image processing steps conducted by the system of FIG. 1.

FIG. 9 shows images I11-I16 associated with six image processing steps conducted by the LabVIEW image processing software implemented on computer 32 of the weld measurement system 10. These images I11-I16 would be presented on the user interface. Image I11 is the first image acquired of the specimen S, which is then corrected for distortion, as described above relative to applying a correction matrix to the initial captured image. In step two, a region of interest (ROI) is chosen in image I12. In step three, image I13 is thresholded and converted from grayscale to binary. In step four, areas of no significance are eliminated from the image I14. Insignificant image features such as small particles, edges, etc., are filtered out of the image I14. At step five, image I15 shows the detected edges of weld buttons W. Based upon the weld button edges detected, the area of the weld buttons W can then be calculated at step six and be displayed proximate each of the weld buttons W in image I16.

Figure 10:
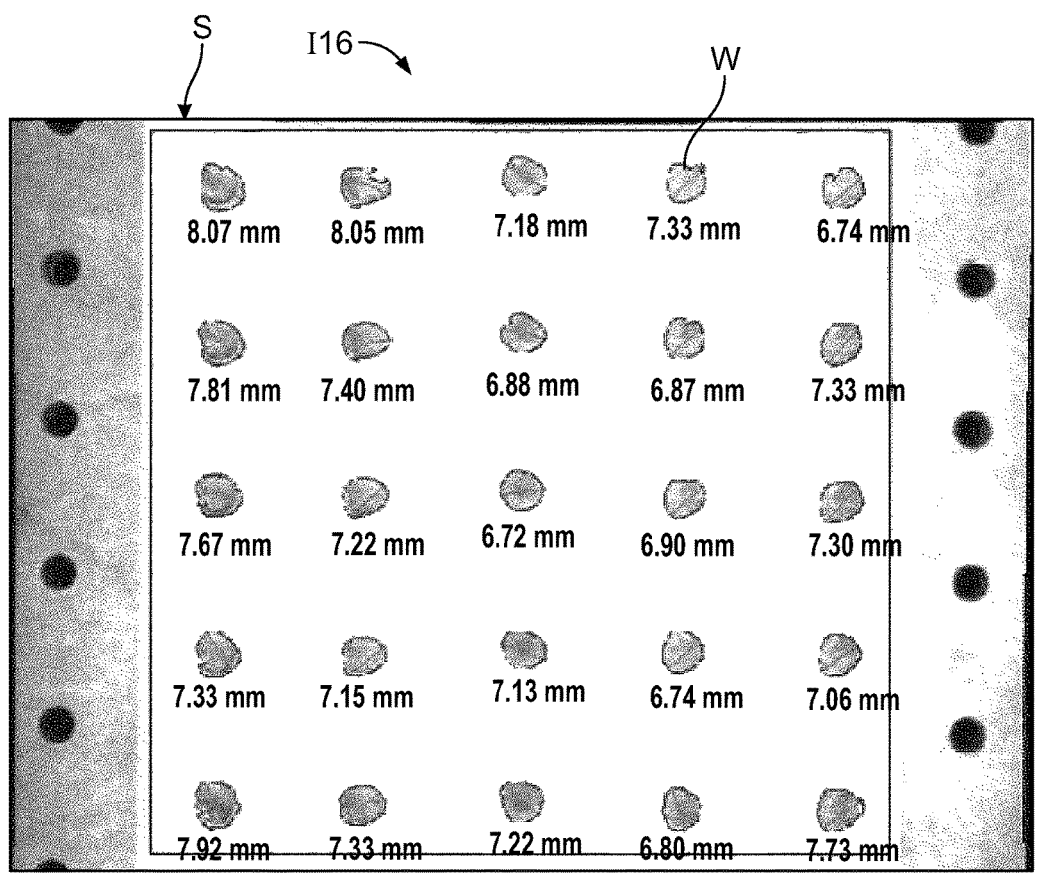
FIG. 10 is an image of a specimen captured by the system of FIG. 1 showing the distance between furthest away points on the edge of each weld button image of the specimen as generated by image analysis by the system of FIG. 1.

FIG. 10 shows an image I16 of a specimen S that has been processed as described above in FIG. 9 and which has been marked by the results of the calculation of the distance between two furthest away points on the edge of each weld button. This calculation is based on the saved mapping matrix. (max Feret diameter). The area of each weld button W that has been calculated is also displayed. This area permits the calculation of the equivalent diameter of a circle with the same area as the button. (Waddle disk diameter). The ratio between the max Feret diameter and the Waddle disk diameter can then be calculated. The image processing algorithm may be developed and implemented using LabVIEW Vision Development Module. LabVIEW (Laboratory Virtual Instrument Engineering Workbench) is a system design platform and development environment for a visual programming language from National Instruments. LabVIEW Vision Development Module provides many basic image processing functions for developers to use to implement their image processing algorithms.

Figure 11:
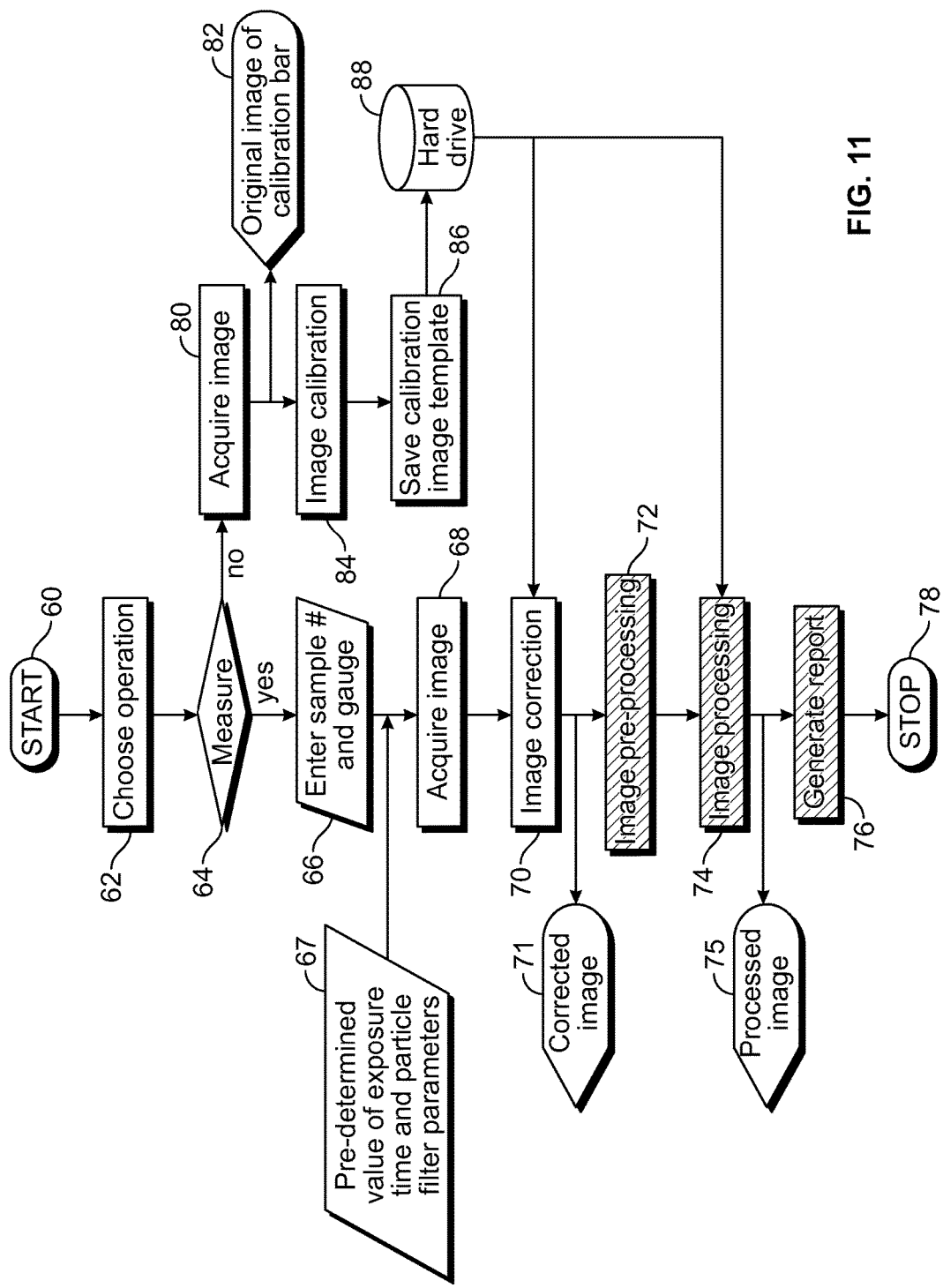
FIG. 11 is a flowchart for the operation of the weld measurement system of FIG.
Figure 13:
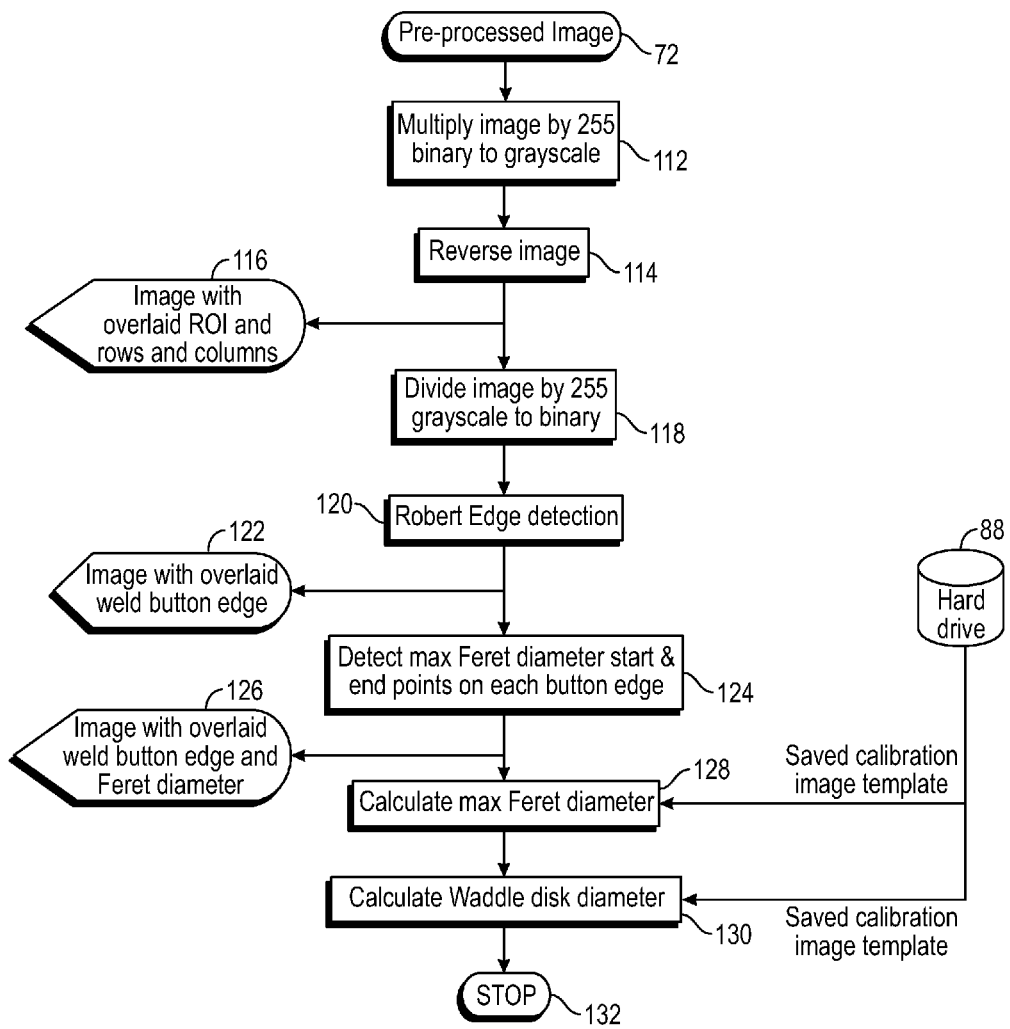
Figure 14:
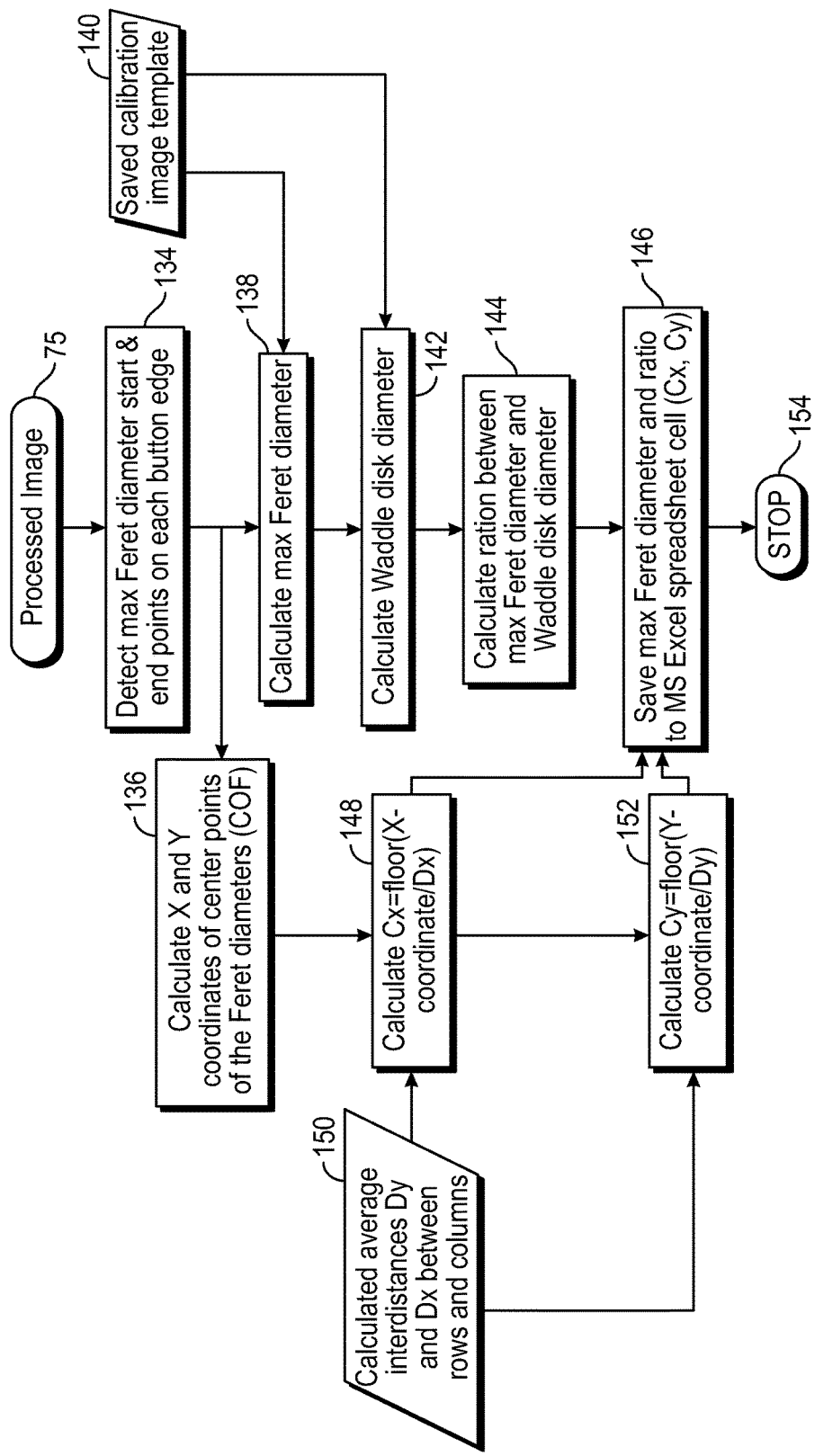

The processing algorithm for processing images acquired by each of the three cameras 14A, 14B, 14C may be the same. FIG. 11 is a high level flowchart showing the steps involved in executing functions of the image processing algorithm. Starting at step 60, the operator chooses the image processing operation that is desired. If the chosen operation is to measure the weld buttons at step 64, then the operator enters the identification number of the specimen and the gauge of the specimen at step 66. The weld measurement system 10 then proceeds to acquire the image by activating the cameras 14A, 14B, 14C at step 68. Prior to acquiring the image at step 68, predetermined values for exposure time and particle filter parameters are retrieved at step 67. Image correction is then conducted at step 70. Step 71 calls the functions shown on the flowchart of FIG. 12. Image preprocessing is conducted at step 72 as shown in FIG. 13. Image processing is conducted at step 74 which is followed by the output of the processed image 75 as shown in the flowchart of FIG. 14. A report is generated at step 76 and then the processing is stopped at step 78. In the event that the operator was not interested in measuring the weld buttons at step 64, the other option of acquiring an image 80 for calibration at step 84 is conducted. This requires that an original image of the calibration bar be recalled 82. The calibrated image template is then saved 86 on hard drive 88 or other storage.

Figure 12:
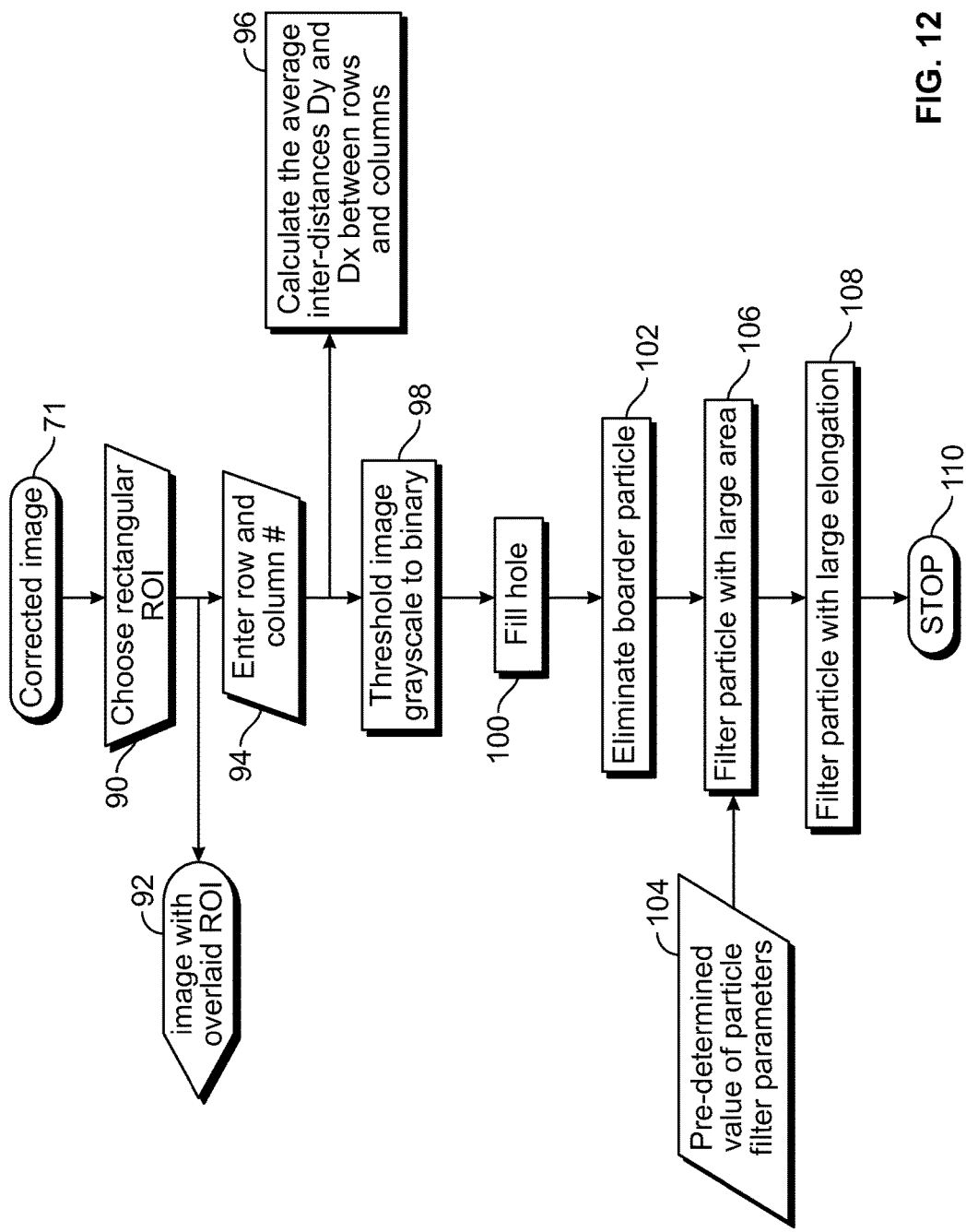
FIGS. 12-14 are detailed flowcharts for functions appearing in the flowchart of FIG. 11.

FIG. 12 expands the steps associated with obtaining a corrected image 71. A rectangular region of the interest (ROI) is chosen at step 90 and the image with overlaid region of interest is output at step 92. The operator then enters the row and column number at step 94. This results in the calculation of the average inter-distances Dy and Dx between rows and columns at step 96. The image is then thresholded from grayscale to binary at step 98. Holes are filled at step 100 and border particles are eliminated at step 102. Using the predetermined value of particle filter parameters 104, the particles with large elongation area are filtered at step 106. Particles with large elongation are filtered at step 108 and the process is stopped at step 110.

FIG. 13 shows an expanded flow chart for the preprocessed image 72. At step 112, the image is multiplied by 255 binary to grayscale. At step 114, a reverse image is created. The image is overlaid with regions of interest and rows and columns provided at step 116. At step 118, the image is divided by 255 grayscale to binary. Robert edge detection is conducted at step 120 and an image with overlaid weld button edges is output at step 122. The max Feret diameter start and end points are detected on each button edge at step 124 and the image with overlaid weld buttons and the max Feret diameter are output at step 126. Using the saved calibration image template from the hard drive 88, the max Feret diameter is calculated at step 128. Then the Waddle disk diameter is calculated at step 130 and the process stopped at 132.

FIG. 14 shows an expanded flow chart pertaining to developing a processed image 75. At step 134, the max Feret diameter is detected, as well as the start and end points on each button edge. This leads to the calculation of the X and Y coordinates of the center points of the max Feret diameters (COF) at step 136. Using the saved calibration image template 140, the max Feret diameter is calculated at step 138. The same calibrated image template 140 is also used to calculate the Waddle disk diameter at step 142. The ratio between the max Feret diameter and the Waddle disk diameter is then calculated at step 144. Using the previously calculated X and Y coordinates of the center points of the max Feret diameters from step 136 and the average inter-distances Dy and Dx between rows and columns calculated at step 150, Cx=floor (X-coordinate/Dx) is calculated at step 148 and Cy=floor (Y-coordinate/Dy) is calculated at step 152. The max Feret diameter and ratio is then saved to an Excel spreadsheet cell (Cx, Cy) at step 146.

Figure 15:
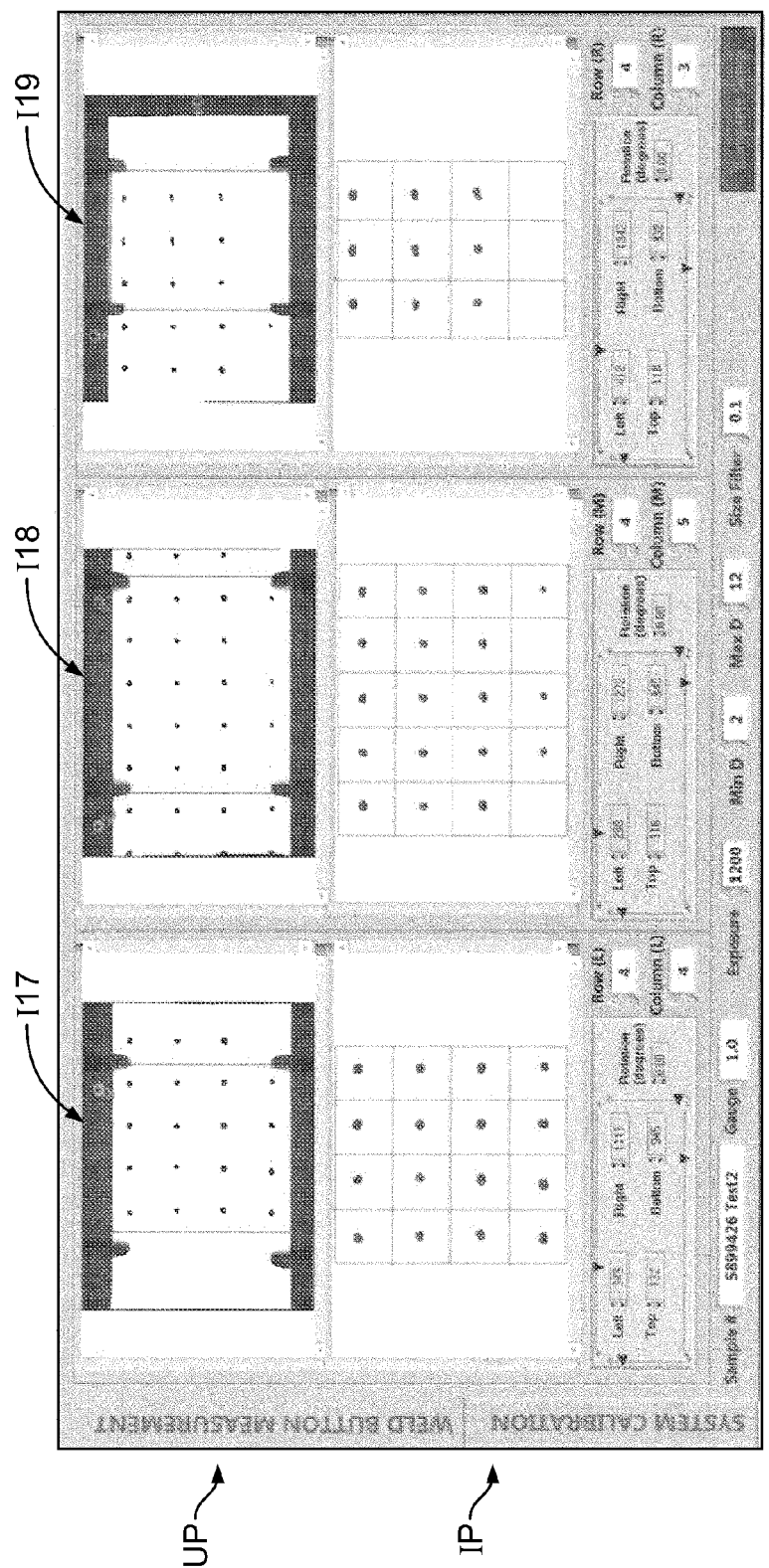
FIG. 15 is a screen shot of a user interface of the weld measurement system of FIG. 1.

FIG. 15 shows that a graphical user interface screen GU1 having fields permitting operator input, e.g. sample number, gauge, exposure, minimum D, maximum D and filter size. The upper portion UP of the display GU1 shows the image that will be acquired of a specimen when image capture is initiated. Three distinct portions I17, I18 and I19 are displayed corresponding to the view of cameras 14A, 14B and 14C. Each image I17, I18, I19 is outlined in red. An intermediate portion of the display IP shows the image processed rows and columns of weld buttons corresponding to the images I17, I18, I19.

Figure 16B:
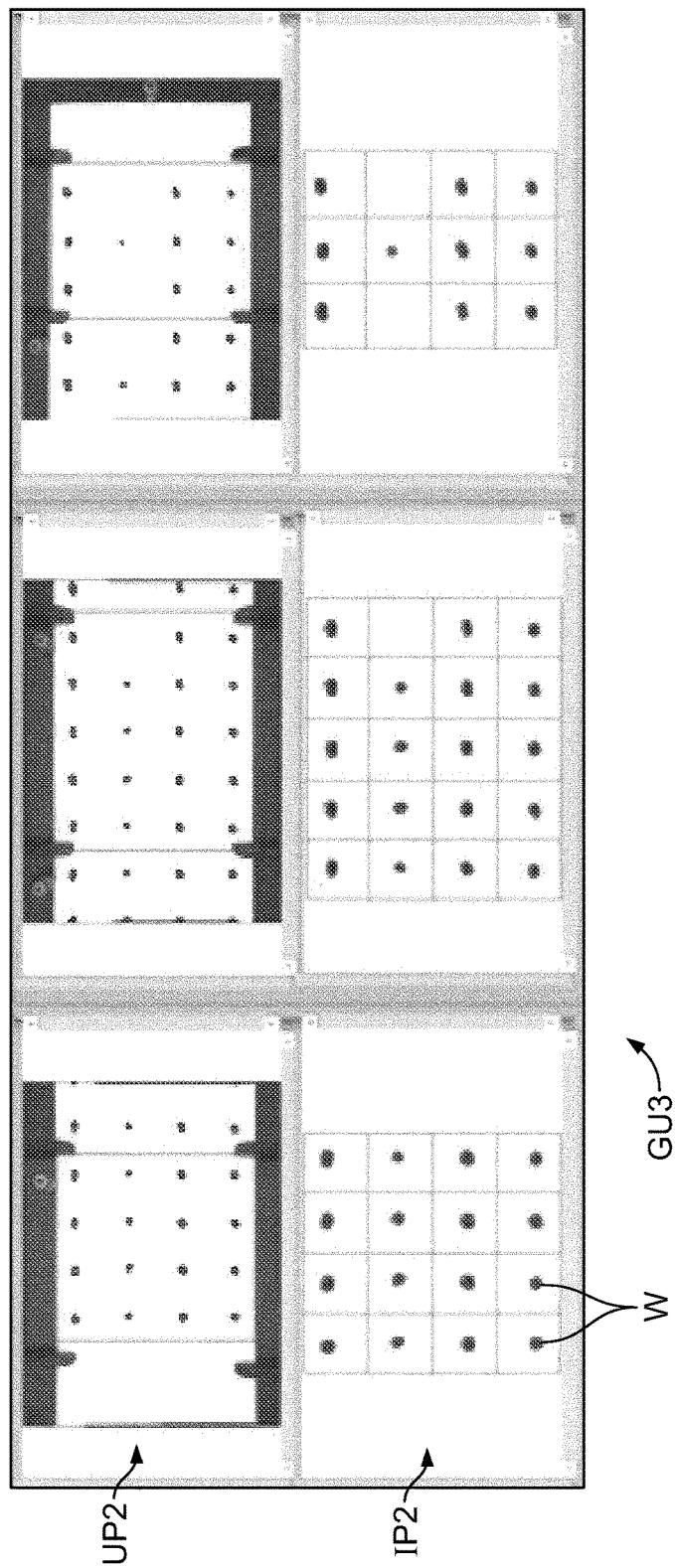
Figure 16C:
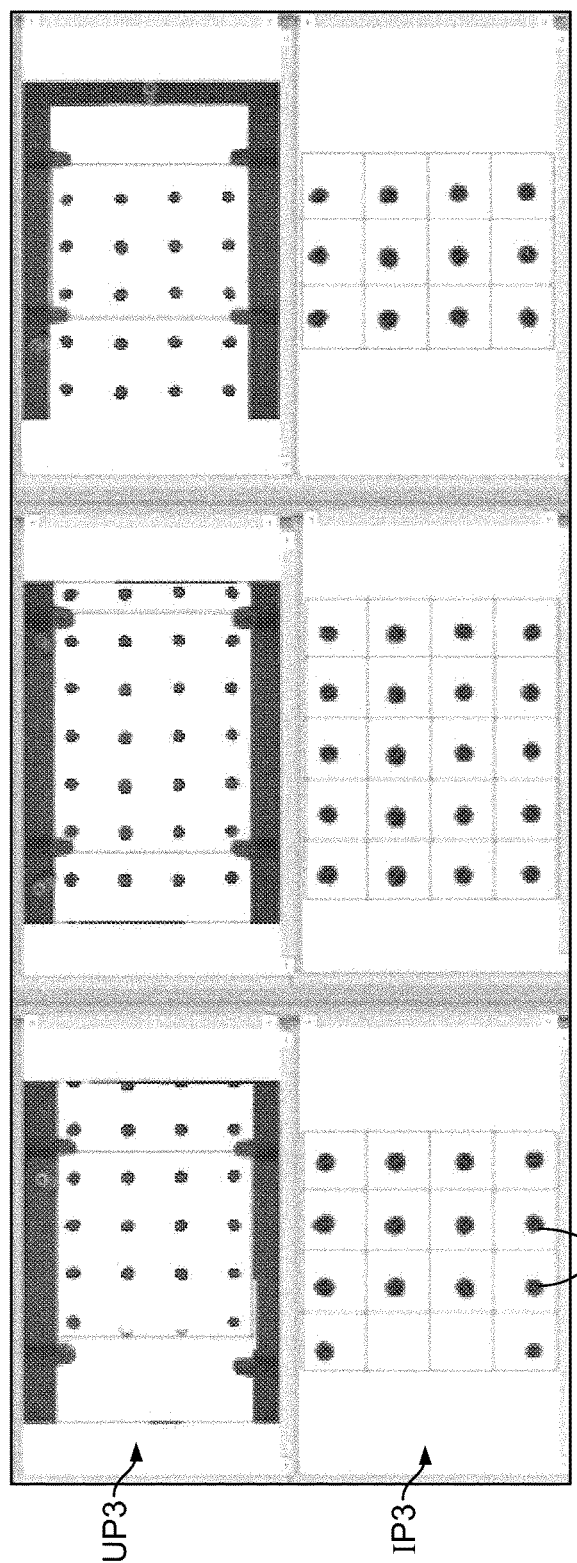

FIGS. 16A, 16B and 16C show the upper portions, UP1, UP2, UP3 and intermediate portions IP1, IP2, IP3 of graphic user interface displays GU2, GU3, GU4 of three different samples, namely 1.0 mm, 2.0 mm and 2.5 mm gauge sheet that has been welded and then separated to measure weld dimensions. As can be appreciated, the gauge of the material welded impacts the size of the welds W, with the larger welds present in the thicker gauges.

Figure 17A:
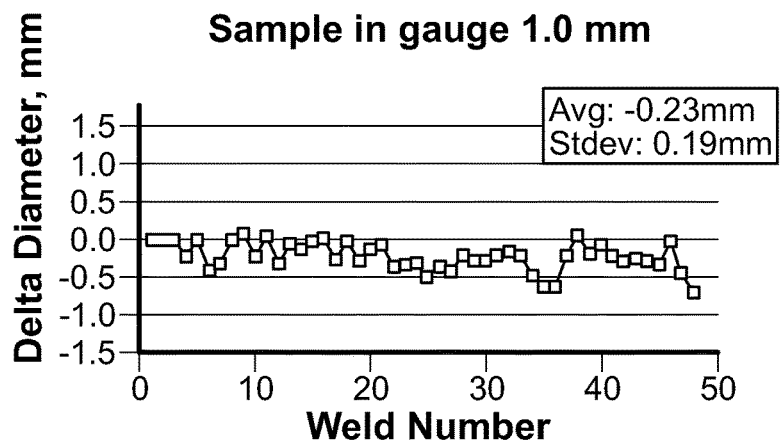
FIGS. 17A-17C are graphs of measurement results generated by the system of FIG. 1 for three different specimens.
Figure 17B:
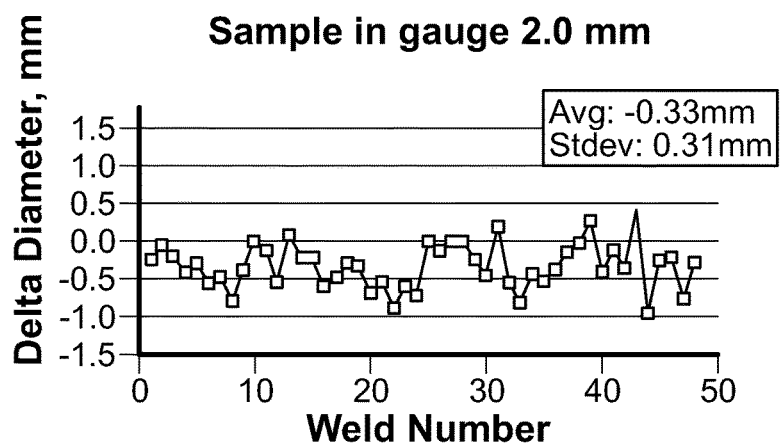
Figure 17C:
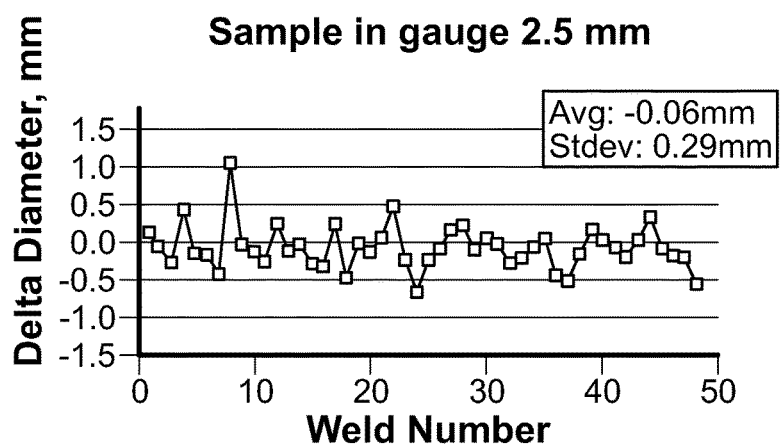

FIGS. 17A, 17B, 17C show reports of weld diameter presented in the form of graphs. The graphs show the number of welds counted for each sample imaged and also the diameters of those welds, calculating the average diameter and the standard deviation, all of which are displayed.

Measurement system 10 consists of both hardware and software. The hardware system includes a linear diffusive dome LED light 18, three GigE cameras 14A, 14B, 14C, a tray table 20T with specially designed clampers 20F for specimen S placement, and a computer 32 for image acquisition, processing, and report generation. A network switch for data transfer may be provided. The software system includes an interface GU1 for image calibration and an interface for system setup, image acquisition and processing. The specimen S for inspection can be simply put on the tray table 20T and clamped so the cameras 14A-C can take three images of different sections of the specimen S simultaneously. The image processing steps measure weld buttons W and automatically generate a report in spreadsheet format. The linear diffusive dome LED light 18 eliminates image saturation and enhances contrast on reflective aluminum sheet.

Three cameras 14A, 14B, 14C covering the entire specimen S allow a single measurement operation that measures all weld buttons at once, keeping measurement accuracy high with low distortion. The slideable specimen support 20 allows the specimen S to be easily loaded and positioned for image acquisition. The tray table 20T, specimen holder 26, and fingers 26F facilitate easy placement of the specimen S on weld measurement system 10. The fingers 26F keep the specimen S flat and enhance the measurement accuracy. The use of calibration specimens SC of un-welded panels with different gauges and with a pattern of dots compensates measurement errors from image distortion and differences in gauge thickness. The weld measurement system 10 may accommodate specimens S with different configurations (number of weld buttons, rows and columns). The image processing steps of the system 10 reduce measurement error introduced by the image of the ring effect from spot welding. The image processing utilizes qualification and quantification methods on the weld button geometry based on the ratio between largest diameter and equivalent diameter of the weld button. The system 10 enables highly repeatable, accurate, 100% inspection of welds almost instantaneously, whereas a benchmark manual method typically measures only 4% of the welds produced.

The system 10 of the present disclosure may be advantageously used in conjunction with an apparatus disclosed in an application filed contemporaneously herewith and owned by the assignee of the present application, entitled, Peeling Apparatus and Method for Separating Welded Layers, such application being incorporated herein by reference in its entirety. The foregoing apparatus may be used to separate a plurality of welded sheets for testing of the welds and for measuring the dimensions thereof. Since the foregoing apparatus separates the sheets leaving at least one in an approximately flat configuration, it may be readily further straightened to yield a substantially flat configuration, e.g., by pressing the separated sheet in a press or by passing it through rollers. As noted above, a flat specimen facilitates consistent imaging due to a consistent distance from the weld buttons to the camera(s) 14A, 14B, 14C that image them, as well as consistent weld button orientation.

It will be understood that the embodiments described herein are merely exemplary and that a person skilled in the art may make many variations and modifications without departing from the spirit and scope of the disclosed subject matter. For example, the positioning elements 20P may be disposed on the tray 20T in a manner customized to receive a particular user's specimen S size. The system 10 may be adapted to a robotic loader/unloader, as well as automation of specimen clamping and specimen support movement for imaging, which may be accomplished by electronic motors under the control of a computer, such as computer 32. A light assembly 18 having a different shape such as circular dome light may be used. The image processing algorithm may be modified to achieve better contrast, etc. All such variations and modifications are intended to be included within the scope of the application.

We claim:

1. A method for inspecting a specimen with at least one bond artifact, comprising:
    positioning a calibration standard with a pattern before a camera;
    illuminating the calibration standard;
    acquiring digital image data of the calibration standard with the camera;
    receiving the digital image data of the calibration standard in a computer;
    further receiving dimension data pertaining to the pattern on the calibration standard in the computer;
    comparing the dimension data and the digital image data, and then calculating a correction matrix to compensate for divergence of the image data of the calibration standard from the dimension data of the calibration standard;
    positioning the specimen before the camera;
    illuminating the specimen;
    acquiring digital image data of the specimen and bond artifact with a camera;
    receiving the digital image data of the specimen from the camera in the computer programmed with an image processing program;
    applying the correction matrix to image data associated with image data of the specimen acquired during the step of acquiring;
    identifying a region of interest in the image data of the specimen;
    thresholding the image of the specimen relative to a criteria value;
    filtering insignificant features from the image of the specimen;
    detecting edges of the at least one bond artifact;
    measuring the area of the at least one bond artifact as represented in the image data; and
    reporting the result of the step of measuring to a user.

2. The method of claim 1, wherein the step of measuring includes calculating the max Feret diameter by identifying the distance between the two furthest away points on the edge of the bond artifact; ascertaining the area of the bond artifact; calculating the Waddle disk diameter of the circle with the same area as the bond artifact and calculating the ratio of the max Feret Diameter to the Waddle Disk diameter.

3. The method of claim 1, further comprising the step of holding the light, the camera and the specimen relative to one another in a framework.

4. The method of claim 3, wherein the framework includes a table that supports the specimen in front of the camera and the light and the step positioning the specimen includes placing the specimen on the table.

5. The method of claim 4, wherein the framework has a specimen holder and further comprising the step of pressing the specimen against the table.

6. The method of claim 5, wherein the specimen holder includes a plurality of inwardly extended fingers mounted on a frame that is configured to be selectively positioned between a position above the specimen and a position pressing the specimen against the table.

7. The method of claim 6, wherein the table is slidably coupled to the framework and is configured to assume a position below the camera and a position distal to the camera permitting the specimen to be placed on the table, pressed down by the fingers and subsequently slid under the camera.

8. The method of claim 1, wherein the light has a diffuser hood with an aperture therein through which a lens of the camera is extended.

9. The method of claim 8, wherein the camera is a first camera and further including at least one additional camera to define a plurality of cameras and wherein the diffuser hood has a plurality of apertures therein for admitting a lens of each of the plurality of cameras there through, each of the plurality of cameras acquiring an image of the specimen within a field of view of the camera during the step of acquiring digital image data of the specimen, the field of view of each camera differing from the field of view of the other cameras of the plurality of cameras.

10. The method of claim 9, wherein the plurality of cameras includes at least three cameras.

11. The method of claim 10, wherein the bond artifact is an artifact of a spot weld and wherein the calibration standard has dimensions allowing the calibration standard to be placed on the table as the specimen is placed, the calibration standard having a plurality of spaced dots approximating a pattern of spot welds.

12. A method for inspecting a specimen with at least one bond artifact, comprising:
  acquiring digital image data of a calibration standard with a camera and receiving the digital image data of the calibration standard in a computer, and further receiving dimension data pertaining to the pattern on the calibration standard and comparing the dimension data and the digital image data;
  calculating a correction matrix to compensate for divergence of the image data from the dimension data;
  applying paint to the at least one bond artifact, the paint increasing the contrast of the bond artifact with the remainder of the specimen proximate the artifact;
  flattening the specimen;
  illuminating the specimen;
  acquiring digital image data of the specimen and the bond artifact with a camera;
  receiving the digital image data of the specimen from the camera into a computer programmed with an image processing program, the computer controlling the camera during the step of acquiring, including a length of exposure of the specimen;
  measuring the at least one bond artifact as represented in the image data; and reporting the result of the step of measuring to a user.

13. The method of claim 12, further comprising the step of applying the correction matrix to image data associated with image data of the specimen acquired during the step of acquiring.

14. The method of claim 13, further comprising the steps of choosing a region of interest in the digital image data acquired during the step of acquiring and filtering insignificant areas from the image data.

15. The method of claim 14, further comprising the steps of detecting an edge of the artifact and calculating the area and the max Feret diameter of the artifact.

16. The method of claim 15, further comprising the steps of thresholding the grayscale values of the image data of the specimen against a pre-determined threshold criteria, filling holes in the image data and eliminating particles with a value less than or equal to the threshold.

17. The method of claim 16, wherein the at least one artifact is a plurality of artifacts of welds and further comprising the steps of generating a report of measurement data on the area of weld artifacts.

* * * * *